United States Patent [19]

Hardy et al.

[11] Patent Number: 4,840,738
[45] Date of Patent: Jun. 20, 1989

[54] STABLE BIODEGRADABLE FABRIC SOFTENING COMPOSITIONS CONTAINING 2-HYDROXYPROPYL MONOESTER QUATERNIZED AMMONIUM SALTS

[75] Inventors: Frederick E. Hardy, Ponteland, United Kingdom; Darlene R. Walley, Cincinnati, Ohio

[73] Assignee: The Procter & Gamble Company, Cincinnati, Ohio

[21] Appl. No.: 160,380

[22] Filed: Feb. 25, 1988

[51] Int. Cl.$^4$ .................. D06M 00/00; C11D 7/08
[52] U.S. Cl. .................................. 252/8.6; 8/137; 252/8.8; 252/142; 252/547; 260/404; 560/1
[58] Field of Search ............... 252/8.6, 8.8, 547, 142

[56] References Cited

U.S. PATENT DOCUMENTS

| | | | |
|---|---|---|---|
| 3,272,712 | 9/1966 | Kalopissis et al. | 167/87 |
| 3,342,840 | 9/1967 | Sobolev | 260/404 |
| 3,442,692 | 5/1969 | Gaiser | 117/120 |
| 3,681,241 | 8/1972 | Rudy | 252/8.75 |
| 3,872,138 | 3/1975 | Ogata | 260/404 |
| 4,022,938 | 5/1977 | Zaki et al. | 427/242 |
| 4,128,485 | 12/1978 | Bauman et al. | 252/8.8 |
| 4,178,256 | 12/1979 | Ciko et al. | 252/8.6 |
| 4,238,531 | 12/1980 | Rudy et al. | 427/242 |
| 4,339,391 | 7/1982 | Hoffmann et al. | 260/401 |
| 4,368,127 | 1/1983 | Richmond | 252/8.8 |
| 4,401,578 | 8/1983 | Verbruggen | 252/8.8 |
| 4,426,299 | 1/1984 | Verbruggen | 252/8.8 |
| 4,661,269 | 4/1987 | Trinh et al. | 252/8.8 |
| 4,701,268 | 10/1987 | Nelson et al. | 252/8.6 |
| 4,767,547 | 8/1988 | Straathof et al. | 252/8.8 |

FOREIGN PATENT DOCUMENTS

| | | |
|---|---|---|
| 1100262 | 5/1981 | Canada . |
| 0018039 | 10/1980 | European Pat. Off. . |
| 0220904 | 5/1987 | European Pat. Off. ............. 252/8.6 |
| 1619043 | 10/1969 | Fed. Rep. of Germany . |
| 1935499 | 1/1971 | Fed. Rep. of Germany . |
| 2430140 | 2/1976 | Fed. Rep. of Germany . |
| 2829022 | 1/1980 | Fed. Rep. of Germany . |
| 49-1510 | 1/1974 | Japan . |
| 1601360 | 10/1981 | United Kingdom . |

Primary Examiner—A. Lionel Clingman
Attorney, Agent, or Firm—Bart S. Hersko; George W. Allen; Richard C. Witte

[57] ABSTRACT

Shelf-stable biodegradable fabric softening compositions are provided comprising mixtures of a quaternized ester-ammonium softening compound having the formula

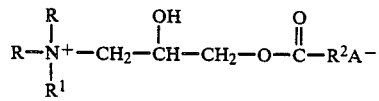

and mixtures thereof, wherein each R substituent is independently selected from $C_1$-$C_6$ alkyl, alkenyl or hydroxyalkyl groups, $R^1$ is a $C_{14}$-$C_{22}$ hydrocarbyl group, $R^2$ is a $C_{13}$-$C_{21}$ hydrocarbyl group, and $A^-$ is a softener compatible anion; and a liquid carrier. These biodegradable compositions have improved product stability and dispersability, as well as excellent fabric softening characteristics.

16 Claims, No Drawings

STABLE BIODEGRADABLE FABRIC SOFTENING COMPOSITIONS CONTAINING 2-HYDROXYPROPYL MONOESTER QUATERNIZED AMMONIUM SALTS

TECHNICAL FIELD

The present invention relates to textile treatment compositions. In particular, it relates to textile treatment compositions for use in the rinse cycle of a textile laundering operation to provide fabric softening/static control benefits, the compositions being characterized by excellent storage stability and viscosity characteristics, as well as biodegradability. The compositions herein can also be used to treat fabrics in hot air clothes dryers and in through-the-wash compositions, as well as in hair conditioner compositions.

BACKGROUND OF THE INVENTION

Textile treatment compositions suitable for providing fabric softening and static control benefits during laundering are well-known in the art and have found widescale commercial application. Conventionally, rinse-added fabric softening compositions contain, as the active softening component, substantially water-insoluble cationic materials having two long alkyl chains. Typical of such materials are di-tallow di-methyl ammonium chloride and imidazolinium compounds subhstituted with two stearyl groups. These materials are normally prepared in the form of a dispersion in water. It is generally not possible to prepare such aqueous dispersions with more than about 10% of cationic materials without encountering intractable problems of product viscosity and stability, especially after storage at elevated temperatures, such that the compositions are unpourable and have inadequate dispensing and dissolving characteristics in rinse water. This physical restriction on softener concentration naturally limits the level of softening performance achievable without using excessive amounts of product, and also adds substantially to the costs of distribution and packaging. Accordingly, it would be highly desirable to prepare physically-acceptable textile treatment compositions containing much higher levels of water-insoluble cationic softener materials.

It would also be desirable to have fabric softening compositions which are storage-stable, and also which are biodegradable. However, materials which may be biodegradable are often difficult to formulate as stable liquid compositions.

It is an object of this invention to provide a storage-stable, biodegradable fabric softening composition. It is a further object to provide such materials in the form of liquid products, including concentrates, suitable for use in the rinse cycle of a textile laundering operation, and in sheet form for use in clothes dryers. These and other objects are obtained using the present invention, as will be seen from the following disclosure.

Cationic softener materials are normally supplied by the manufacturer in the form of a slurry containing about 70%–80% of active material in an organic liquid such as isopropanol, sometimes containing a minor amount of water (up to about 10%). Retail fabric softening compositions are then prepared by dispersion of the softener slurry in warm water under carfully controlled conditions. The physical form and dispersibility constraints of these industrial concentrates, however, are such as to preclude their direct use by the domestic consumer; indeed, they can pose severe processing problems even for the industrial supplier of retail fabric softening compositions.

The use of various quaternized ester-amines as cationic fabric softening agents is known in the art. See, for example, U.S. Pat. No. 4,339,391, Hoffmann, et al., issued July 13, 1982, for a series of quaternized ester-amines which function as fabric softeners. Various quaternized ester-amines are commercially available under the tradenames SYNPROLAM FS from lCl and REWOQUAT from REWO. Similarly, methods for preparing various quaternized ester-amine compounds are known in the art. See, for example, U.S. Pat. No. 3,342,840, Sobolev, issued Sept. 19, 1967, U.S. Pat. No. 3,872,138, Ogatu, issued Mar. 18, 1975, and Japanese Laid Open Publication No. 49-1510, assigned to Gosei Chem. Ind. Co., published Jan. 9, 1974.

Unfortunately, although quaternized ester-amines are believed to be rapidly biodegradable, they are more subject to hydrolysis than are conventional cationic softening agents (e.g., ditallow dimethyl ammonium chloride and analogs thereof) and hence can encounter hydrolytic stability problems upon prolonged shelf storage. The product stability and viscosity problems becoming increasingly more unmanageable in concentrated aqueous dispersions.

Various solutions to the problem of preparing concentrated fabric softening compositions suitable for consumer use have been addressed in the art. See, for example, U.S. Pat. Nos. 4,426,299, issued Jan. 17, 1984, and 4,401,578, issued Aug. 30, 1983, Verbruggen, which relate to paraffin, fatty acids and ester extenders in softener concentrates as viscosity control agents.

European Patent No. 0,018,039, Clint, et al., issued Mar. 7, 1984, relates to hydrocarbons plus soluble cationic or nonionic surfactants in softener concentrates to improve viscosity and stability characteristics.

U.S. Pat. No. 4,454,049, MacGilp, et al., issued June. 12, 1984, discloses concentrated liquid textile treatment compositions in the form of isotropic solutions comprising water-insoluble di-$C_{16}$–$C_{24}$ optionally hydroxy-substituted alkyl, alkaryl or alkenyl cationic fabric softeners, at least about 70% of the fabric softener consisting of one or more components together having a melting completion temperature of less than about 20° C., a water-insoluble nonionic extender, especially $C_{10}$–$C_{40}$ hydrocarbons or esters of mono- or polyhydric alcohols with $C_8$–$C_{24}$ fatty acids, and a water-miscible organic solvent. The concentrates have improved formulation stability and dispersibility, combined with excellent fabric softening characteristics.

U.S. Pat. No. 4,439,330, Ooms, issued Mar. 27, 1984, teaches concentrated fabric softeners comprising ethoxylated amines.

U.S Pat. No. 4,476,031, Ooms, issued Oct. 9, 1984, teaches ethoxylated amines or protonated derivatives thereof, in combination with ammonium, imidazolinium, and like materials. The use of alkoxylated amines, as a class, in softener compositions is known (see, for example, German Patent Applications Nos. 2,829,022, Jskobi and Schmadel, published Jan. 10, 1980, and 1,619,043, Mueller et al., published Oct. 30, 1969, and U.S. Pat. Nos. 4,076,632, Davis, issued Feb. 28, 1978, and 4,157,307, Jaeger and Davis, issued June 5, 1979).

U.S. Pat. No. 4,422,949, Ooms, issued Dec. 27, 1983, relates to softener concentrates based on ditallow dimethyl ammonium chloride (DTDMAC), glycerol monostearate and polycationcs.

In United Kingdom Application No. 2,007,734A, Sherman et al., published May 23, 1979, fabric softener concentrates are disclosed which contain a mixture of fatty quaternary ammonium salts having at least one $C_8$–$C_{30}$ alkyl substituent and an oil or substantially water-insoluble compound having oily/fatty properties. The concentrates are said to be easily dispersed/emulsified in cold water to form fabric softening compositions.

Concentrated dispersions of softener mateerial can be prepared as described in European Patent Application No. 406 and United kingdom Patent Specification No. 1,601,360, Goffinet, published Oct. 28, 1981, by incorporating certain nonionic adjunct softening materials therein.

As can be seen, the various solutions to the specific problem of preparing fabric softening compositions in concentrated form suitable for consumer use have not been entirely satisfactory. It is generally known (for example, in U.S. Pat. No. 3,681,241, Rudy, issued Aug. 1, 1972) that the presence of ionizable salts in softener compositions does help reduce viscosity, but this approach is ineffective in compositions containing more than about 12% of dispersed softener, inasmuch as the level of ionizable salts necessary to reduce viscosity to any substantial degree has a seriously detrimental effect on product stability.

It has now been discovered that fabric softener compositions, especially concentrated compositions, containing the specific quaternized hydroxypropyl monoester ammonium salts of the present invention possiss desirable product stability and viscosity characteristics. Moreover, neither the use of these specific compounds in laundry fabric softening compositions, nor the desirable fabric softener/viscosity/stability/biodegradability properties of fabric softening compositions containing these compounds, including concentrates, appear to have been appreciated heretofore.

SUMMARY OF THE INVENTION

The present invention relates to a shelf-stable/biodegradable fabric softening composition comprising:

(a) from about 1% to about 20% by weight of a quaternized ester-ammonium softening compound having the formula

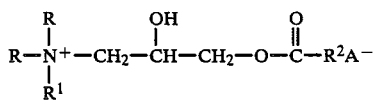

and mixtures thereof, wherein each R substituent is independently selected from $C_1$–$C_6$ alkyl, alkenyl or hydroxyalkyl groups, $R^1$ is a $C_{14}$–$C_{22}$ hydrocarbyl group, $R^2$ is a $C_{13}$–$C_{21}$ hydrocarbyl group, and $A^-$ is a softener compatible anion; and (b) from about 60% to about 98% of a liquid carrier, e.g., water, preferably a mixture of a $C_1$–$C_4$ monohydric alcohol and water.

While not intending to be limited by theory, it is believed that the ester moiety lends biodegradability to these compounds, whereas the fact that only a single ester group is present provides sufficient hydrolytic stability that the compounds can be stably formulated as liquid compositions, under the conditions disclosed hereinafter. The desirable viscosity characteristics of the compounds which allows them to be formulated as concentrates are unexpected. Moreover, since the compounds are cationic, they provide not only fiber and fabric softness, but also anti-static benefits.

The liquid compositions of the present invention are preferably formulated at a pH of from about 2.0 to about 5.0 to provide good storage stability.

The preferred liquid compositions herein have the softening compound present as particles dispersed in the liquid carrier. The particles are preferably sub-micron size, generally having average diameters in the range of about 0.10–0.50 microns. Such particle dispersions can optionally be stabilized against settling by means of standard non-base emulsifiers, especially nonionic extenders.

Importantly, the liquid compositions herein are substantially free (generally, less than about 1%) of free (i.e., unprotonated) amines, since free amines can catalyze decomposition of the quaternized ester-ammonium softening compouns, on storage. If minor amounts of amines are present, they should be protonated with acid during the formulation of the compositions. Strong acids, such as $H_3PO_4$ and HCl, can be used for this purpose.

The low viscosities exhibited by dispersions of particles of the softening compounds described herein allow them to be formulated as water-dilutable fabric softener "high concentrates" which contain from about 11% to about 20% by weight of the fabric softener compound. Such high concentrates may be conveniently packaged in pouches, which can be diluted with water by the user to produce "single-strength" softeners (typically, 3–8% concentration of softener active).

The compounds herein can also be formulated as solids, for example, in combination with particulate carriers as particulate fabric softening and antistatic compositions. When formulated as solids, the pH and presence or absence of amines are, of course, not as critical as with the liquid compositions, since stability to hydrolysis on storage is not so problematic.

Other solid compositions herein the compounds releasably affixed to sheet materials to provide fabric softening and antistatic compositions in sheet form which can be used in hot air clothes dryers.

The inventtion also encompsses a method of softening fibers (including hair) or fabrics, or imparting an antistatic finish thereto, comprising contacting said fibers or fibers with a composition of the above-disclosed type. All percentages, ratios and proportions All percentages, ratios and proportions herein are by weight, unless otherwise specified.

DETAILED DESCRIPTION OF THE INVENTION

The compositions of the present invention comprise a mixture of a quaternary ester-ammonium fabric softening compound and a liquid carrier.

Quaternized Ester-Ammonium Softening Compound

The present invention contains as an essential component from about 1% to about 20%, preferably from about 2% to about 10%, of a quaternized ester-ammonium softening compound having the formula

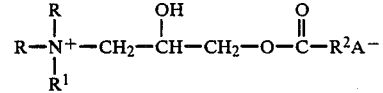

wherein each R substituent is a short chain ($C_1$-$C_6$, preferably $C_1$-$C_3$) alkyl, alkenyl or hydroxyalkyl group, e.g., methyl (most preferred), ethyl, propyl, propenyl, hydroxyethyl, and the like, or mixtures thereof; $R^1$ is a long chain $C_{14}$-$C_{22}$ hydrocarbyl substituent, preferably $C_{16}$-$C_{18}$alkyl, most preferably straight-chain $C_{18}$ alkyl; $R^2$ is a long chain $C_{13}$-$C_{21}$ hydrocarbyl substituent, preferably $C_{13}$-$C_{17}$ alkyl, most preferably $C_{17}$ straight chain alkyl. The counterion $A^-$ is not critical herein, and can be any softener-compatible anion, for example, chloride, bromide, methylsulfate, formate, sulfate, nitrate and the like. It will be understood that substituents R, $R^1$ and $R^2$ may optionally be substituted with various groups such as alkoxyl, hydroxyl, or can be branched, but such materials are not preferred herein. In addition, R, $R^1$ and $R^2$ may optionally be unsaturated (i.e., R, $R^1$ and/or $R^2$ may be alkenyl groups). The preferred compounds can be considered to be a 2-hydroxypropyl monoester variation of ditallow dimethyl ammonium salts (e.g., DTDMAC, a widely used fabric softener compound).

The above compounds used as the active softener and antistatic ingredient in the practice of this invention are prepared using standard reaction chemistry. For example, in a preferred method of synthesis, a fatty acid of the formula $R^2COOH$ is neutralized with a tertiary amine of the formula $R^1N(R)_2$ and made into a fatty acid-tertiary ammonium salt which is then reacted with epichlorohydrin to yield the desired reaction product (wherein R, $R^1$ and $R^2$ are as defined above). A method for the synthesis of a preferred softening compound is disclosed in detial hereinafter. However, it will be appreciated by those skilled in the chemical arts that this reaction sequence allows a broad selection of compounds to be prepared.

Illustrative, nonlimiting examples of useful quaternized 2-hydroxypropyl monoester ammonium salts (wherein all long-chain alkyl substituents are straight-chain) include:

[CH$_3$]$_2$[C$_{18}$H$_{37}$]$^{\oplus}$NCH$_2$CH(OH)CH$_2$OC-(O)C$_{17}$H$_{35}$Br$^{\ominus}$

[CH$_3$]$_2$[C$_{16}$H$_{33}$]$^{\oplus}$NCH$_2$CH(OH)CH$_2$OC-(O)C$_{15}$H$_{31}$Cl$^{\ominus}$

[C$_2$H$_5$]$_2$[C$_{18}$H$_{35}$]$^{\oplus}$NCH$_2$CH(OH)CH$_2$OC-(O)C$_{15}$H$_{31}$Cl$^{\ominus}$

[C$_2$H$_5$][CH$_3$][C$_{18}$H$_{37}$]$^{\oplus}$NCH$_2$CH(OH)CH$_2$OC-(O)C$_{17}$H$_{35}$CH$_3$SO$_4$$^{\ominus}$

[C$_3$H$_7$][C$_2$H$_5$][C$_{16}$H$_{33}$]$^{\oplus}$NCH$_2$CH(OH)CH$_2$OC-(O)C$_{15}$H$_{31}$Cl$^{\ominus}$

[iso-C$_3$H$_7$][CH$_3$][C$_{18}$H$_{37}$]$^{\oplus}$NCH$_2$CH(OH)CH$_2$OC-(O)C$_{15}$H$_{31}$I$^{\ominus}$ Since the foregoing compounds are somewhat labile to hydrolysis, they should be handled rather carefully when used to formulate the compositions herein. For example, stable liquid compositions herein are formulated at a pH in the range of about 2.0 to about 5.0, preferably about pH 3.5±0.5. The pH can be adjusted by the addition of a Bronsted acid. Examples of suitable Bronsted acids include the inorganic mineral acids, carboxylic acids, in particular the low molecular weight ($C_1$-$C_5$) carboxylic acids, and alkylsulfonic acids. Suitable inorganic acids include HCl, $H_2SO_4$, $HNO_3$ and $H_3PO_4$. Suitable organic acids include formic, acetic, methylsulfonic and ethylsulfonic acid. Preferred acids are hydrochloric and phosphoric acids.

Synthesis of quaternized monoester amine softening compound

Synthesis of the preferred biodegradable, quaternized monoester ammonium softening compound used herein can be accomplished using the following "one-pot" process:

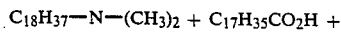
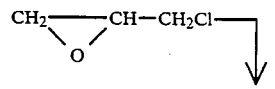
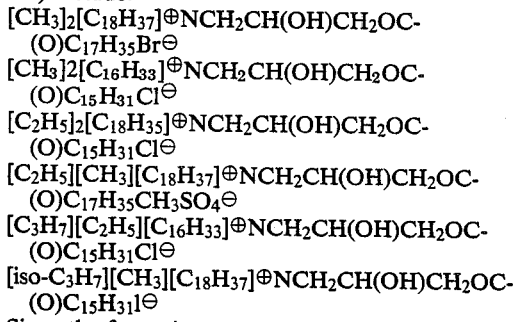

50 g (0.175 mole) of stearic acid and 80 g of isoproanol are placed in a 3-necked, 500-ml round bottom flask equipped with a reflux condenser, and mixed with a magnetic stir bar. 52.7 g (0.175 mole) of dimethyl stearyl amine is added to the stirring stearic acid-isopropanol mixture, followed by the addition of 30 g of water. The mixture is stirred for approximately ½ hour (until a clear solution is obtained). Next, 18.4 g (0.190 mole) of epichlorohydrin is added to the mixture. The temperature is raised to 80° C. (oil bath) and the stirring is continued for an additional 20 hours.

The reaction mixture is cooled to room temperature, and a white precipitate is formed. The solid material is collected on a Whatman ® #1 filter paper (using a Buchi funnel apparatus) and is subsequently recrystallized from hot (60° C.) isopropanol. solid material is dried under vacuum (0.2 mm Hg) for 24 hours.

ANALYSIS

TLC (thin layer chromatography): 10×20 cm glass plate, 250 micron silica gel; solvent system, chloroform-:methanol:water (15:6:0.6; v/v/v); visualization, 5% phosphomolybdic acid in ethanol; Rf=0.61.

IR (CCl$_4$): 3140, 2920, 2850, 1958, 1724, 1525, 1464, 1210, 1170cm$^{-1}$.

$^1$HNMR (CDCl$_3$): δ6.02 (1H), 4.6–4.4 (1H), 4.3–40 (2H), 3.7–3.3 (10H), 2.3 (2H), 1.8–1.4. (4H), 1.2 (58H), 0.8 (6H), ppm (relative to tetramethylsilane).

$^{13}$CNMR (CDCl$_3$): δ173.4, 66.4, 66.0, 65.9, 63.5, 52.5, 52.4, 34.3, 31.9, 29.7, 29.5, 29.3, 29.2, 26.6, 25.0, 22.7, 22.6, 14.1 ppm (relative to tetramethylsilane).

Liquid Carrier

The compositions herein comprise a liquid carrier, e.g., water, preferably a mixture of water and a $C_1$-$C_4$ monohydric alcohol (e.g., ethanol, propanol, isopropoanol, butanol, and mixtures thereof), isopropanol being preferred. These compositions comprise from about 60% to about 98%, preferably from about 70% to about 95%, of the liquid carrier. Preferably, the amount of the $C_1$-$C_4$ monohydric alcohol in the liquid carrier is from about 5% to about 50% by weight of the quaternized ester-ammonium softening compound, the balance of the liquid carrier being water.

The softening compounds used in this invention are insoluble in such water-based carriers and, thus, are present as a dispersion of fine particles therein. These particles are sub-micron, preferably having average diameters of from about 0.1 to about 0.5 microns, in size and are conveniently prepared by high-shear mixing which disperses the compounds as fine particles. A method of preparation of a preferred dispersion is disclosed in detail in Examples I–IV hereinafter. Again, since the softening compounds are hydrolytically labile, care should be taken to avoid the presence of base, and to keep the processing temperatures and pH within the ranges specifed herein.

The particulate dispersions of the foregoing type can optionally be stabilized against settling by means of standard non-base emulsifiers, especially nonionic extenders. Such nonionics and their usage levels, have been disclosed in U.S. Pat. No. 4,454,049, MacGilp, et al., issued June 12, 1984, the disclosure of which is incorporated herein by reference.

Specific examples of nonionic extenders suitable for use in the compositions herein include glycerol ester (preferably glycerol monostearate), fatty alcohols (e.g., stearyl alcohol), and ethoxylated linear alcohols (preferably Neodol 23-3—the condensation product of $C_{12}$-$C_{13}$ linear alcohol with 3 moles ethylene oxide, marketed by Shell Chemical Company) and mixtures thereof. Mixtures of glycerol monostearate and Neodol 23-3 are particularly preferred. The nonionic, if used, is typically used at a level of from about 0.1% to about 10% by weight of the composition.

Optional Ingredients

Fully-formulated fabric softening compositions may optionally contain, in addition to the rapidly biodegradable quaternary 2-hydroxypropyl monoester ammonium compounds of the formula herein, and liquid carrier, one or more of the following ingredients.

Conventional quaternary ammonium softening agents

The compositions of the present invention can further comprise a conventional di(higher alkyl) quaternary ammonium softening agent. The compositions herein can contain from 0% to about 25% (preferably from about 0.1% to about 10% ) of the conventional di(- higher alkyl) quaternary ammonium softening agent.

By "higher alkyl", as used in the context of the conventional quaternary ammonium salts herein, is meant alkyl groups having from about 8 to about 30 carbon atoms, preferably from about 11 to about 22 carbon atoms. Examples of such conventional quaternary ammonium salts include:

(i) acyclic quaternary ammonium salts having the formula:

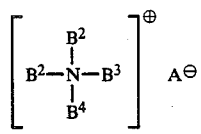

wherein $B^2$ is an acyclic aliphatic $C_{15}$-$C_{22}$ hydrocarbon group, $B^3$ is a $C_1$-$C_4$ saturated alkyl or hydroxyalkyl group, $B^4$ is selected from $B^2$ and $B^3$, and A is an anion;

(ii) diamido quaternary ammonium salts having the formula:

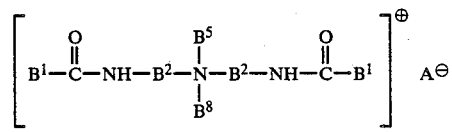

wherein $B^1$ is an acyclic aliphatic $C_{15}$-$C_{22}$ hydrocarbon group, $B^2$ is a divalent alkylene group having 1 to 3 carbon atoms, $B^5$ and $B^8$ are $C_1$-$C_4$ saturated alkyl or hydroxyalkyl groups, and A is an anion;

(iii) diamido alkoxylated quaternary ammonium salts having the formula:

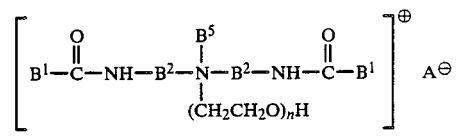

wherein n is equal to from about 1 about 5, and $B^1$, $B^2$, $B^5$ and A are as defined above;

(iv) quaternary imidazolinium compounds having the formula:

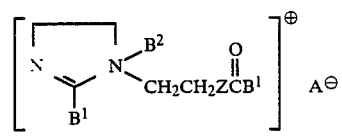

wherein $B^1 = C_{15}$-$C_{17}$ saturated alkyl, $B^2 = C_1 = C_4$ saturated alkyl or H, Z=NH or O, and A is an anion.

Examples of Component (i) are the well-known dialkyldimethylammonium salts such as ditallowdimethylammonium chloride, ditallowdimethylammonium methylsulfate, di(hydrogenated tallow) dimethylammonium chloride, dibehenyldimethylammonium chloride.

Examples of Components (ii) and (iii) are methylbis(tallowamidoethyl) (2-hydroxyethyl) ammonium methylsulfate and methylbis(hydrogenated tallowamidoethyl) (2-hydroxyethyl) ammonium methylsulfate, wherein $B^1$ is an acyclic aliphatic $C_{15}$-$C_{17}$ hydrocarbon group, $B^2$ is an ethylene group, $B^5$ is a methyl group, $B^8$ is a hydroxyalkyl group and A is a methylsulfate anion; these materials are available from Sherex Chemical Company under the trade names Varisoft ® 222 and Varisoft ® 110, respectively.

Examples of Component (iv) are 1-methyl-1-tallowamino-ethyl-2-tallowimidazolinium methylsulfate and 1-methyl-1-(hydrogenated tallowamidoethyl)-methylsulfate.

Free amines

The liquid compositions herein should be substantially free (generally less than about 1%) of free (i.e., unprotonated) amines.

Minor amounts of protonated amines, typically from about 0.05% to about 1.0%, namely primary, secondary and tertiary amines having, at least, one straight-chain organic group of from about 12 to about 22 carbon atoms may be used in the compositions of the present invention to enhance dispersion stability. Preferred amines of this class are ethoxyamines, such as monotallow-dipolyethoxyamine, having a total of from about 2 to about 30 ethoxy groups per molecule. Also suitable are diamines such as tallow-N,N', N'-tris (2-hydroxyethyl)-1,3-propylenediamine, or $C_{16}$-$C_{C18}$-alkyl-N-bis(2-hydroxyethyl) amines. Examples of the above compounds are those marketed under the trade names GENAMIN C, S, O and T, by Hoechst.

Care must be taken that if minor amounts of these amines are used to enhance the dispersion stability of the compositions, they are protonated with acid during formulation, otherwise the free amines may catalyze decomposition of the biodegradable quaternary ammonium compounds during storage.

Di-(higher alkyl) cyclic amine

The compositions herein optionally comprise from 0% to about 25% (preferably from about 0.1% to about 10%) by weight of the composition of a di(higher alkyl) cyclic amine fabric softening agent of the formula:

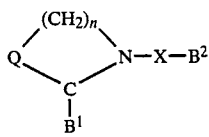

wherein n is 2 or 3, preferably 2; $B^1$ and $B^2$ are, independently, a $C_8$-$C_{30}$ alkyl or alkenyl, preferably $C_{11}$-$C_{22}$ alkyl, more preferably $C_{15}$-$C_{18}$ alkyl, or mixtures of such alkyl radicals. Examples of such mixtures are the alkyl radicals obtained from coconut oil, "soft" (non-hardened) tallow, and hardened tallow. Q is CH or N, preferably N.

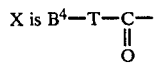

wherein T is O or $NB^5$, $B^5$ being H or $C_1$-$C_4$ alkyl, preferably H, and $B^4$ is a divalent $C_1$-$C_3$ alkylene group or $(C_2H_4O)_m$, wherein m is from about 1 to about 8.

Silicone Component

The fabric softening compositions herein optionally contain an aqueous emulsion of a predominantly linear polydialkyl or alkyl aryl siloxane in which the alkl groups can have from one to five carbon atoms and may be wholly or partially fluorinated. These siloxanes act to provide improved fabric feel benefits. Suitable silicones are polydimethyl siloxanes having a viscosity, at 25° C., of from about 100 to about 100,000 centistokes, preferably from about 1,000 to about 12,000 centistokes.

It has been found that the ionic charge characteristics of the silicone as used in the present invention are important in determining both the extent of deposition and the evenness of distribution of the silicone and hence the properties of a fabric treated therewith.

Silicones having cationic character show an enhanced tendency to deposit. Silicones found to be of value in providing fabric feel benefits having a predominantly linear character and are preferably polydialkyl siloxanes in which the alkyl group is most commonly methyl. Such silicone polymers are frequently manufactured commercially by emulsion polymerization using a strong acid or strong alkali catalyst in the presence of a nonionic or mixed nonionic anionic emulsifier system. In addition to providing improved fabric feel benefits, the silicone components also improve the water absorbency of the fabrics treated with the softening compositions herein.

The optional silicone component embraces a silicone of cationic character which is defined as being one of:
(a) a predominantly linear di-$C_1$-$C_5$ alkyl or $C_1$-$C_5$ alkyl aryl siloxane, prepared by emulsion polymerization using a cationic or nonionic surfactant as emulsifier;
(b) an alpha-omega-di-quaternized di-$C_1$-$C_5$ alkyl or $C_1$-$C_5$ alkyl aryl siloxane polymer; or
(c) an amino-functional di-$C_1$-$C_5$ alkyl or alkyl aryl siloxane polymer in which the amino group may be substituted and may be quaternized and in which the degree of substitution (d.s.) lies in the range of from about 0.0001 to about 0.1, preferably from about 0.01 to about 0.075
provided that the viscosity at 25° C. of the silicone is from about 100 to about 100,000 cs.

The fabric softening compositions herein may contain up to about 15%, preferably from about 0.1% to about 10%, of the silicone component.

Thickening Agent

Optionally, the compositions herein contain from 0% to about 3%, preferably from about 0.01% to about 2%, of a thickening agent. Examples of suitable thickening agents include: cellulose derivatives, synthetic high molecular weight polymers (e.g., carboxyvinyl polymer and polyvinyl alcohol), and cationic guar gums.

The cellulosic derivatives that are functional as thickening agents herein may be characterized as certain hydroxyethers of cellulose, such as Methocel ®, marketed by Dow Chemicals, Inc.; also, certain cationic cellulose ether derivatives, such as Polymer JR-125 ®, JR-400 ®, and JR-30M ®, marketed by Union Carbide.

Other effective thickening agents are cationic guar gums, such as Jaguar Plus ®, marketed by Stein Hall, and Gendrive 458 ®, marketed by General Mills.

Preferred thickening agents herein are selected from the group consisting of methyl cellulose, hydroxypropyl methylcellulose, hydroxybutyl methylcellulose, or mixtures thereof, said cellulosic polymer having a viscosity in 2% aqueous solution at 20° C. of from about 75,000 centiposie.

Soil Release Agent

Optionally, the compositions herein contain from 0% to about 10%, preferably from about 0.2% to about 5%, of a soil release agent. Preferably, such a soil release agent is a polymer. Polymeric soil release agents useful in the present invention include copolymeric blocks of terephathalate and polyethylene oxide or polypropylene oxide, and the like.

A preferred soil release agent is a copolymer having blocks of terephthalate and polyethylene oxide. More specifically, these polymers are comprised of repeating units of ethylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weight of from about 300 to about 2000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between 2:1 and 6:1. Examples of this polymer include the commercially available materials Zelcon ® 4780 (from Dupont) and Milease ® T (from ICI).

Highly preferred soil release agents are polymers of the generic formula:

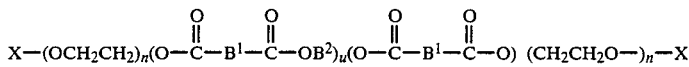

in which X can be any suitable capping group, with each X being selected from the group consisting of H, and alkyl or acyl groups containing from about 1 to about 4 carbon atoms. n is selected for water solubility and generally is from about 6 to about 113, preferably from about 20 to about 50. u is critical to formulation in a liquid composition having a relatively high ionic strength. There should be very little material in which u is greater than 10. Furthermore, there should be at least 20, preferably at least 40, of material in which u ranges from about 3 to about 5.

The $B^1$ moieties are essentially 1,4-phenylene moieties. As used herein, the term "the $B^1$ moieties are essentially 1,4-phenylene moieties" refers to compounds where the $B^1$ moieties consist entirely of 1,4-phenylene moieties, or are partially substituted with otherarylene or alkarylene moieties, alkylene moieties, alkenylene moieties, or mixtures thereof. Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene and mixtures thereof. Alkylene and alkenylene moieties which can be partially substituted include ethylene, 1,2-propylene, 1,4-butylene, 1,5-pentylene, 1,6-hexamethylene, 1,7-heptamethylene, 1,8-octamethylene, 1,4-cyclohexylene, and mixtures thereof.

For the $B^1$ moieties, the degree of partial substitution with moieties other than 1,4-phenylene should be such that the soil release properties of the compound are not adversely affected to any great extent. Generally, the degree of partial substitution which can be tolerated will depend upon the backbone length of the compound, i.e., longer backbones can have greater partial substitution for 1,4-phenylene moieties. Usually, compounds where the $B^1$ comprise from about 50% to about 100% 1,4-phenylene moieties (from 0 to about 50% moieties other than 1,4-phenylene) have adequate soil release activity. For example, polyesters made according to the present invention with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $B^1$ moieties consist entirely of (i.e., comprise 100%) 1,4-phenylene moieties, i.e., each $B^1$ moiety is 1,4-phenylene.

For the $B^2$ moieties, suitable ethylene or substituted ethylene moieties include ethylene, 1,2-propylene, 1,2-butylene, 1,2-hexylene, 3-methoxy-1,2-propylene and mixtues thereof. Preferably, the $B^2$ moieties are essentially ethylene moieties, 1,2-propylene moieties or mixture thereof. Inclusion of a greater percentage of ethylene moieties tends to improve the soil release activity of compounds. Surprisingly, inclusion of a greater percentage of 1,2-propylene moieties tends to improve the water solubility of the compounds.

Therefore, the use of 1,2-propylene moieties or a similar branched equivalent is desirable for incorporation of any substantial part of the soil release component in the liquid fabric softener compositions. Preferably, from about 75% to about 100%, more preferably from about 90% to about 100%, of the $B^2$ moieties are 1,2-propylene moieties.

The value for each n is at least about 6, and preferably is at least about 10. The value for each n usually ranges from about 12 to about 113. Typically, the value for each n is in the range of from about 12 to about 43.

A more complete disclosure of these highly preferred soil release agents is contained in European Patent Application No. 185,427, Gosselink, published June 25, 1986, incorporated herein by reference.

Viscosity Control Agents

Viscosity control agents can be used in the compositions of the present invention (preferably in concentrated compositions). Examples of organic viscosity modifiers are fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides of the group IA and IIA metals of the Periodic Table of the Elements, e.g., calcium chloride, magnesium chloride, sodium chloride, potassium bromide, and lithium chloride. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 3,000 parts per million (ppm), preferably from about 20 to about 2,000 ppm, by weight of the composition.

Bactericides

Examples of bactericides used in the compositions of this invention include glutaraldehyde, formaldehyde, 2-bromo-2-nitro-propane-1,3- diol sold by inolex Chemicals under the trade name Bronopol ® and a mixture of 5-chloro-2-methyl-4-isothiazolin-3-one and 2-methyl-4-isothiazoline-3-one sold by Rohm and Haas Company under the trade name Kathon ® CG/ICP. Typical levels of bacteriocides used in the present compositions are from about 1 to about 1,000 ppm by weight of the composition.

Other Optional Ingredients

The present invention can include other optional components conventionally used in textile treatment compostions, for example, colorants, perfumes, preservatives, optical brighteners, opacifiers, fabric conditioning agents, surfactants, stabilizers such as gum and polyethylene glycol, anti-shrinkage agents, anti-wrinkle agents, fabric crisping agents, spotting agents, germicides, fungicides, anti-oxidants such as butylated hydroxy toluene, anti-corrosion agents, and the like.

In the method aspect of this invention, fabrics or fibers (including hair) are contacted with an effective amount, generally from about 20 ml to about 300 ml (per 3.5 kg of fiber or fabric being treated), of the compositions herein in an aqueous bath. Of course, the amount used is based upon the judgement of the user, depending on concentration of the composition, fiber or fabric type, degree of softness desired, and the like. Typically, about 120 mls. or a 5% dispersion of the softening compounds are used in a 25 l laundry rinse bath to soften and provide antistatic benefits to a 3.5 kg load of mixed fabrics. Preferably, the rinse bath contains from about 25 ppm to about 100 ppm of the fabric softening compositions herein.

Solid carrier materials can be used in place of liquids. For example, the softener compounds herein can be absorbed on particulate solids such as potassium sulfate, micronized silica, powdered urea, and the like, and added to a laundry rinse bath. Alternatively, the softeners can be releasably padded onto a sheet (e.g., paper toweling, nonwoven fabric, or the like) and tumbled with damp fabrics in a hot-air clothes dryer, in the manner of the BOUNCE® brand dryer-added product known in commercial practice. Generally, such solid-form compositions will comprise from about 1% to about 20% of the quaternized ester-ammonium softening compound, and from about 75% to about 99% of the solid carrier.

The following examples illustrate the practice of the present invention but are not intended to be limiting thereof.

EXAMPLE I

A storage stable biodegradable fabric softening composition of the present invention is made as follows:

| Ingredient | Percent (wt.) |
|---|---|
| $(CH_3)_2\overset{+}{\underset{\underset{C_{18}H_{37}}{|}}{N}}-CH_2-\overset{\overset{OH}{|}}{CH}-CH_2O\overset{\overset{O}{\|}}{C}-C_{17}H_{35}Cl^-$ | 5.0% |
| Isopropanol | 1.0% |
| Bronopol | 0.01% |
| Dye | 20 ppm |
| 0.1 N HCl | 0.25% |
| Water | Balance |

20 g of the biodegradable monoester ammonium softener compound and 5 g of isopropanol are mixed and heated to 80° C. to form a fluidized "melt". The molten mixture is then poured into a 400 g water seat with high shear mixing. The water is preheated to 70° C., and 20 ppm blue dye and 100 ppm bronopol are added to the water prior to mixing. About 1 g of isopropanol is evaporated from the molten mixture before it is poured into the water. The dispersion is mixed for 25 minutes at 7000 rpm (Tekmar high shear mixer). During mixing the temperature of the dispersion is manintained within 70°–75° C. by a cooling water bath. The pH is adjusted by the addition of 1 ml of 0.1N HCl. The resulting dispersion has a viscosity of 50 centipoise (at 25° C.), a pH of 3.5, and contains less than 1% of free (i.e., unprotonated) amines. The average particle size in the dispersion is 0.20 microns.

EXAMPLE II

A storage stable biodegradable fabric softening composition of the present invention is made as follows:

| Ingredient | Percent (wt.) |
|---|---|
| $(CH_3)_2\overset{+}{\underset{\underset{C_{18}H_{37}}{|}}{N}}-CH_2-\overset{\overset{OH}{|}}{CH}-CH_2O\overset{\overset{O}{\|}}{C}-C_{17}H_{35}Cl^-$ | 5.0% |
| Isopropanol | 1.1% |
| Glyceryl Monostearate (GMS) | 1% |
| Neodol 23-3 | 1% |
| 0.1 N HCl | 0.25% |
| Water | Balance |

20 g of the biodegradable monoester ammonium softener compound and 5 g of isopropanol are mixed and heated to 60° C. to form a fluidized "melt". 4 g of GMS and 4 g of Neodol 23-3 are then added to the melt to form a homogeneous molten mixture. The molten mixture is then poured into a 365 g water seat with high shear mixing. The water is preheated to 50° C. 0.6 g of isopropanol is evaporated from the molten mixture before it is poured into the water. The dispersion is mixed for 20 minutes at 7200 rpm (Tekmar high shear mixer). The pH is adjusted by the addition of 1 ml of 0.1N HCl. The resulting dispersion has a viscosity of 48 centipoise (at 25° C.), a pH of 3.5, and contains less than 1% of free (i.e., unprotonated) amines. The average particle size is 0.17 micron.

EXAMPLE III

A storage stable biodegradable fabric softening composition of the present invention is made as follows:

| Ingredient | Percent (wt.) |
|---|---|
| $(CH_3)_2\overset{+}{\underset{\underset{C_{18}H_{37}}{|}}{N}}-CH_2-\overset{\overset{OH}{|}}{CH}-CH_2O\overset{\overset{O}{\|}}{C}-C_{17}H_{35}Cl^-$ | 4.5% |
| Isopropanol | 0.6% |
| Glyceryl Monostearate (GMS) | 1.2% |
| Neodol 23-3 | 0.3% |
| Polydimethylsiloxane (PDMS) | 0.1% |
| 0.1 N HCl | 0.25% |
| Water | Balance |

18 g of the biodegradable monoester ammonium softener compound and 2.4 g of isopropanol are mixed and heated to 70° C. to form a fluidized "melt". 4.8 g of GMS and 1.2 g of Neodol 23-3 are then added to the melt to form a homogeneous molten mixture. The molten mixture is then poured into a 375 g water seat with high shear mixing. The water is preheated to 65° C. The dispersion is mixed for 15 minutes at 7000 rpm (Tekmar high shear mixer). After the dispersion cools down to about to about 30° C., 0.4 g of PDMS is added to the dispersion with low shear mixing (3000 rpm for 3 minutes). The pH is adjusted by the addition of 1 ml of 0.1N HCl. The resulting dispersion has a viscosity of 88 centipoise (at 25° C.), a pH of 3.9, and contains less than 1% free (i.e., unprotonated) amines. The average particle size in the dispersion is 0.19 microns.

EXAMPLE IV

A storage stable biodegradable concentrated fabric softening composition of the present invention is made as follows:

| Ingredient | Percent (wt.) |
|---|---|
| $(CH_3)_2 - \overset{+}{\underset{\underset{C_{18}H_{37}}{|}}{N}} - CH_2 - \overset{\underset{|}{OH}}{CH} - CH_2 O \overset{\overset{O}{\|}}{C} - C_{17}H_{35} Cl^-$ | 15.0% |
| Isopropanol | 2.5% |
| Glycerol Monostearate (GMS) | 1.0% |
| Neodol 23-3 | 0.5% |
| CaCl$_2$ | 0.06% |
| 0.1 N HCl | 0.25% |
| Water | Balance |

30 g of the biodegradable monoester ammonium softener compound and 5 g of isopropanol are mixed and heated to 75° C. to form a fluidized melt. 2 g of GMS and 1 g of Neodol 23-3 are then added to the melt to form a homogeneous molten mixture. The melt is then poured into a 165 g water seat with high shear mixing. The water is preheated to 60° C. The dispersion is mixed for 15 minutes at 7000 rpm (Tekmar high shear mixer). 6 ml of 2% CaCl$_2$ aqueous solution is added to the dispersion during mixing to prevent the dispersion from gelling. During mixing the dispersion's temperature is maintained at about 60° C. The pH is adjusted by the addition of 0.5 ml of 0.1N HCl. The resulting dispersion has a viscosity of 210 centipoise (at 25° C.), a pH of 3.8, and contains less than 1% free (i.e., unprotonated) amines. The average particle size in the dispersion is 0.26 microns.

In a convenient mode, this concentrated composition is packaged in a simple plastic pounch, which is opened and poured into 4× its volume of water prior to use to prepare a "single strength" softener composition, thereby saving on packaging and shipping costs, as well as storage space.

Typically, the liquid fabric softening compositions in the above examples are added to the rinse cycle of conventional washing machines. When multiple rinses are used, the fabric softening composition is preferably added to the final rinse. The amount added to the rinse cycle is generally from about 20 ml to about 300 ml (per 3.5 kg of fabric being treated) of the compositions of Examples I-III (and the diluted version of Example IV).

EXAMPLE V

The preparation of a fabric-softener sheet for use in a hot-air clothes dryer is as follows:

| | Percent (wt.) |
|---|---|
| Fabric Conditioning Composition Components | |
| $(CH_3)_2 - \overset{+}{\underset{\underset{C_{18}H_{37}}{|}}{N}} - CH_2 - \overset{\underset{|}{OH}}{CH} - CH_2 O \overset{\overset{O}{\|}}{C} - C_{17}H_{35} CH_3SO_4^-$ | 46.0% |
| Sorbitan Monostearate | 46.0% |
| Clay | 7.0% |
| Perfume | 1.0% |
| Dryer-added Sheet Substrate Composition | |
| Rayon fibers | 70.0% |
| Polyvinyl acetate | 30.0% |
| (10" × 14" (25.4 cm × 35.6 cm) sheets, 1.4 gm) | |

The biodegradable monoester ammonium softener compound, sorbitan monostearate, clay (Bentolite L, a montmoillonite clay, obtained from Southern Clay Products), and perfume are mixed and heated to 80° C. to form a fluidized "melt". The substrate (made of the rayon fibers with polyvinyl acetate) is then coated with about 4 grams of the molten actives and dried overnight. This provides a weight ratio of fabric conditioning composition:dry substrate of approximately 3.

Following solidification of the fabric conditioning composition, the substrate is slit with a knife, said slits being in substantially parallel relationship and extending to within about 1 inch (2.5 cm from at least one edge of said substrate. The width of an individual slit is approximately 0.2 inches (0.5 cm ). These dryer added sheets are added to a clothes dryer together with damp fabrics to be treated (typically, one sheet per 3.5 kg load of fabrics, dry with basis). The heat and tumbling action of the revolving dryer drums evenly distributes the composition over all fabrics, and dries the fabrics. Fabric softening and static control are provided to the fabrics in this manner.

In all of the above examples, substantially similar results are obtained when the biodegradable quaternary monoester ammonium softening compound is replaced, in whole or in part, with any of the following biodegradable monester ammonium softening compounds:

[CH$_3$]$_2$[C$_{18}$H$_{37}$]$^\oplus$NCH$_2$CH(OH)CH$_2$OC-(O)C$_{17}$H$_{35}$Br$^\ominus$

[CH$_3$]$_2$[C$_{16}$H$_{33}$]$^\oplus$NCH$_2$CH(OH)CH$_2$OC-(O)C$_{15}$H$_{31}$Cl$^\ominus$

[C$_2$H$_5$]$_2$[C$_{18}$H$_{35}$]$^\oplus$NCH$_2$CH(OH)CH$_2$OC-(O)C$_{15}$H$_{31}$Cl$^\ominus$

[C$_2$H$_5$][CH$_3$ ][C$_{18}$H$_{37}$$^\oplus$NCH$_2$CH(OH)CH$_2$OC-(O)C$_{17}$H$_{35}$CH$_3$SO$_4$$^\ominus$

[C$_3$H$_7$][C$_2$H$_5$][C$_{16}$H$_{33}$]$^\oplus$NCH$_2$CH(OH)CH$_2$OC-(O)C$_{15}$H$_{31}$Cl$^\ominus$

[iso-C$_3$H$_7$][CH$_3$][C$_{18}$H$_{37}$]$^\oplus$NCH$_2$CH(OH)CH$_2$OC-(O)C$_{15}$H$_{31}$I$^\ominus$ Importantly, the above biodegradable liquid compositions (Examples I-IV) display excellent softening characteristics on both normal and elevated temperatures, and good product stability and dispersibility.

What is claimed is:

1. A liquid fabric softening and antistatic composition comprising:
   (a) from about 1% to about 20% by weight of submicron-sized particles of a quaternized ester-ammonium softening compound having the formula $$R - \overset{\overset{R}{|}}{\underset{\underset{R^1}{|}}{N^+}} - CH_2 - \overset{\overset{OH}{|}}{CH} - CH_2 - O - \overset{\overset{O}{\|}}{C} - R^2 A^-$$

and mixtures therof, wherein each R substitutent is independently selected from C$_1$-C$_6$ alkyl, alkenyl or hydroxyalkyl groups, R$_1$ is a C$_{14}$-C$_{22}$ hydrocarbyl group, R$^2$ is a C$_{13}$-C$_{21}$ hydrocarbyl group and, A$^-$ is a softener compatible anion; and
   (b) from about 60% to about 98% of a liquid carrier having said softening compound particles dispersed therein; said compositions being maintained at a pH ranging from about 2.0 to about 5.0 and further being substantially free of unprotonated amines.

2. A composition according to claim 1 wherein each R substituent is $C_1$-$C_3$ alkyl, $R^1$ is $C_{16}$-$C_{18}$ alkyl, and $R^2$ is $C_{13}$-$C_{17}$ alkyl.

3. A composition according to claim 2 wherein each R substituent is methyl.

4. A composition according to claim 3 which contains from about 2% to about 10% of the softening compound.

5. A composition according to claim 1 which is formulated at a pH of about 3.0±0.5.

6. A composition according to claim 2 wherein the liquid carrier consists of a mixture of (i) $C_1$-$C_4$ monohydric alcohol or mixtures thereof; and (ii) water;

the amount of monohydric alcohol being from about 5% to about 50% by weight of the softening compound.

7. A composition according to claim 6 wherein the particles have an average diameter of from 0.1 to about 0.5 micron.

8. A composition according to claim 7 wherein the monohydric alcohol is isopropanol.

9. A composition according to claim 1 which additionally contains from about 0.1% to about 10% of a conventional di-(higher alkyl) quaternary ammonium softening agent.

10. A composition according to claim 1 which additionally contains from about 0.1% to about 10% by weight of a nonionic extender.

11. A composition according to claim 10 wherein the nonionic extender is selected from the group consisting of glycerol esters, fatty alcohols, ethoxylated linear alcohols, and mixtures thereof.

12. A composition according to claim 5 wherein the quaternized ester-ammonium softening compound is

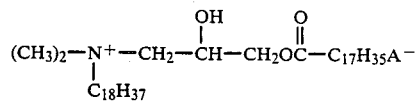

13. A composition according to claim 1 in concentrated form which contains from about 11% to about 20% of the softening compound.

14. A composition according to claim 13 which additionally contains from about 20 to about 3,000 ppm of a salt selected from the group consisting of calcium chloride, magnesium chloride, sodium chloride, potassium chloride, lithium chloride, and mixtures thereof.

15. A composition according to claim 14 wherein the salt is calcium chloride.

16. A method of softening and providing an antistatic finish to fabrics by contacting said fabrics with an effective amount of the composition of claim 1.

* * * * *

UNITED STATES PATENT AND TRADEMARK OFFICE
CERTIFICATE OF CORRECTION

PATENT NO. : 4,840,738

DATED : June 20, 1989

INVENTOR(S) : Frederick E. Hardy and Darlene R. Walley

It is certified that error appears in the above-identified patent and that said Letters Patent is hereby corrected as shown below:

Column 1, lines 28 & 29, "subhstituted" should be --substituted--.

Column 4, line 45, "inventtion" should be --invention--.

Column 4, line 45, "encomposses" should be --encompasses--.

Column 5, line 32, "detial" should be --detail--.

Column 7, line 12, "ester" should be --esters--.

Column 9, line 33, "alkl" should be --alkyl--.

Column 11, line 15, "20" should be --20%-- and "40" should be --40%--.

Column 11, line 21, "otherarylene" should be --other arylene--.

Column 12, line 58, "gum" should be --guar gum--.

Column 16, line 19, "with" should be --weight--.

UNITED STATES PATENT AND TRADEMARK OFFICE
CERTIFICATE OF CORRECTION

PATENT NO. : 4,840,738

DATED : June 20, 1989

INVENTOR(S) : Frederick E. Hardy and Darlene R. Walley

It is certified that error appears in the above-identified patent and that said Letters Patent is hereby corrected as shown below:

Column 16, line 44, insert after the word both the following:
--natural and synthetic fabrics, low viscosity at both--.

Signed and Sealed this

Seventh Day of April, 1992

Attest:

HARRY F. MANBECK, JR.

*Attesting Officer*      *Commissioner of Patents and Trademarks*